US011399990B2

(12) United States Patent
Suyama

(10) Patent No.: US 11,399,990 B2
(45) Date of Patent: Aug. 2, 2022

(54) ABSORBENT PAD

(71) Applicant: DAIO PAPER CORPORATION, Ehime (JP)

(72) Inventor: Junnosuke Suyama, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 454 days.

(21) Appl. No.: 16/493,012

(22) PCT Filed: Mar. 6, 2018

(86) PCT No.: PCT/JP2018/008473
§ 371 (c)(1),
(2) Date: Sep. 11, 2019

(87) PCT Pub. No.: WO2018/173736
PCT Pub. Date: Sep. 27, 2018

(65) Prior Publication Data
US 2020/0008987 A1 Jan. 9, 2020

(30) Foreign Application Priority Data

Mar. 21, 2017 (JP) .............................. JP2017-055038

(51) Int. Cl.
*A61F 13/531* (2006.01)
*A61F 13/539* (2006.01)
(Continued)

(52) U.S. Cl.
CPC .......... *A61F 13/531* (2013.01); *A61F 13/539* (2013.01); *A61F 13/5323* (2013.01);
(Continued)

(58) Field of Classification Search
CPC ................ A61F 13/5323; A61F 2013/530481
(Continued)

(56) References Cited

U.S. PATENT DOCUMENTS 5,030,314 A * 7/1991 Lang ...................... B32B 37/24
19/144
5,643,238 A * 7/1997 Baker ............... A61F 13/53752
604/378
(Continued)

FOREIGN PATENT DOCUMENTS

JP     S59159420 U    10/1984
JP     2011120710 A * 6/2011 ....... A61F 13/49473
(Continued)

OTHER PUBLICATIONS

Translation of International Search Report dated May 15, 2018 and Written Opinion of corresponding application No. PCT/JP2018/008473; 10 pgs.

*Primary Examiner* — Susan S Su
(74) *Attorney, Agent, or Firm* — Maier & Maier, PLLC

(57) ABSTRACT

To provide an absorbent pad, the absorbent pad being formed of an inner absorbent pad which is positioned on the body-side and an outer absorbent pad positioned on the non-body side, wherein when the inner absorbent pad absorbs liquid excretions and swells, openings are provided at the side which is indented furthest towards the non-body side, improving the passage of liquid, and improving the dispersion of sites facing the openings in the outside absorbent pad, preventing leakage of liquid excretions to the exterior.

13 Claims, 12 Drawing Sheets

(51) Int. Cl.
*A61F 13/532* (2006.01)
*A61F 13/53* (2006.01)

(52) U.S. Cl.
CPC ............ *A61F 2013/530131* (2013.01); *A61F 2013/530226* (2013.01); *A61F 2013/530343* (2013.01); *A61F 2013/530481* (2013.01)

(58) Field of Classification Search
USPC .................................................. 604/358–392
See application file for complete search history.

(56) References Cited

U.S. PATENT DOCUMENTS

| | | | |
|---|---|---|---|
| 2007/0197987 A1* | 8/2007 | Tsang ................ | A61F 13/15699 604/368 |
| 2015/0148766 A1* | 5/2015 | Nakakado ........... | B29C 66/7373 156/580.2 |
| 2015/0182386 A1* | 7/2015 | Nakakado ........... | B32B 37/0076 156/199 |
| 2017/0165131 A1* | 6/2017 | Varona ................ | A61F 13/5323 |

FOREIGN PATENT DOCUMENTS

| | | | | |
|---|---|---|---|---|
| JP | 2015-112401 A | | 6/2015 | |
| JP | 2015-150056 A | | 8/2015 | |
| WO | WO-9511651 A1 * | 5/1995 | ......... | A61F 13/5323 |
| WO | WO-02056809 A2 * | 7/2002 | ......... | A61F 13/5323 |
| WO | WO-2016148194 A1 * | 9/2016 | ....... | A61F 13/51104 |
| WO | WO-2017022655 A1 * | 2/2017 | ........... | A61F 13/532 |

\* cited by examiner

ABSORBENT PAD

FIELD

The present invention relates to absorbent pads used for absorbent articles such as disposable diapers and sanitary napkins and pads.

BACKGROUND

Traditionally, a prior art proposes a technique of forming an absorbent pad for a disposable diaper using a liquid-permeable front sheet, a liquid-permeable rear sheet and an absorbent polymer in between the front sheet and the liquid-permeable rear sheet and providing opening sections extending along the longitudinal direction of connecting parts extending in the longitudinal direction at predetermined intervals in the width direction and opening sections extending along the width direction of connecting parts extending in the width direction at predetermined intervals in the longitudinal direction to absorbent pads when viewed in plan. (Patent Document 1)

Another prior art proposes a technique of forming an absorbent pad for a disposable diaper using an inner absorbent pad formed by absorbent polymers and positioned on the body side and an outer absorbent pad formed by absorbent polymers and pulp fibers, providing opening sections extending in the longitudinal direction at the center of the inner absorbent pad in the width direction, and providing a higher pulp fiber density to the opposite site of the opening sections of the outer absorbent pad located on the lower side than other sites. (Patent Document 2)

[Patent Document 1] Japanese Unexamined Patent Publication No. 2015-112401

[Patent Document 2] Japanese Unexamined Patent Publication No. 2015-150056

SUMMARY

However, according to the technique of Patent Document 1, when the absorbent pad swells by absorbing the liquid excretions, there is a risk of leaking the excess liquid excretions that did not absorb into the absorbent pad to outside since the opening sections are not provided to the most indented sites of the non-body side.

Further, according to the technique of Patent Document 2, due to the small size of the sites with high pulp fiber density formed to the lower side of the absorbent pad than the opening sections of the upper side of the absorbent pad, the liquid excretions transferring from the opening sections of the upper absorbent pad to the lower absorbent pad do not quickly diffuse to the lower absorbent pad, and therefore, there is a risk of leaking the liquid excretions transferring to the lower absorbent pad to outside.

In view of the foregoing, the subject of the invention is to provide an absorbent pad formed with an inner absorbent pad positioned on the body side and an outer absorbent pad positioned on the non-body side, wherein the liquid permeability is improved by providing opening sections at the most indented sites on the non-body side in case the upper absorbent pad swells by absorbing the liquid excretions, and the leakage of the liquid excretions to outside is prevented by improving the diffusibility of the opposite sites of the opening sections of the outer absorbent pad.

The subject of the invention has been achieved and disclosed as the following:

A first aspect of the present invention is directed to an absorbent pad that an inner absorbent pad positioned on the body side and an outer absorbent pad positioned on the non-body side are layered, the inner absorbent pad is formed with a liquid-permeable first front sheet, a liquid-permeable first rear sheet and absorbent polymer particles absorbing the liquid excretions that are provided in between the liquid-permeable first front sheet and the liquid-permeable first rear sheet, the first front sheet and the first rear sheet are connected with first junctions extending in the longitudinal direction at predetermined intervals in the width direction and second junctions extending in the width direction at predetermined intervals in the longitudinal direction when viewed in plan, the absorbent polymer particles are packed within cells defined by an adjacent pair of the first junctions and an adjacent pair of the second junctions, and opening sections are formed at intersections where the first junctions and second junctions intersect.

A second aspect of the present invention is, as in the embodiment of the first aspect, that the opening sections formed at the center in the longitudinal direction of the inner absorbent pad are made smaller than the opening sections formed in the front and rear sides in the longitudinal direction of the inner absorbent pad.

A third aspect of the present invention is, as in the embodiment of the first aspect or the second aspect, that the opening sections are formed in the rectangle configurations and providing the long sides of the rectangles along with the first junctions when viewed in plan.

A fourth aspect of the present invention is, as in the embodiment of the third aspect, that the dimension of the long side of the rectangles is formed longer than the width in the longitudinal direction of the second junctions when viewed in plan.

A fifth aspect of the present invention is, as in the embodiment of any one of the first, second, third or fourth aspect, that the outer absorbent pad is formed with the absorbent core constituting the liquid-permeable second front sheet, the liquid-permeable or liquid-impermeable second rear sheet and pulp fibers and absorbent polymer particles absorbing the liquid excretions provided in between the second front sheet and the second rear sheet, the high fiber density areas are arranged with higher pulp fiber density than the adjacent sections to the opposite sites of the opening sections of the outer absorbent pad, and the opening sections are layered on the high fiber density area when viewed in plan.

A sixth aspect of the present invention is, as in the embodiment of any one of the first, second, third or fourth aspect, that the outer absorbent pad is formed with the liquid-permeable third front sheet, the liquid-permeable or liquid-impermeable third rear sheet and the absorbent polymer particles absorbing the liquid excretions and being placed in between the third front sheet and the third rear sheet, the third front sheet and the third rear sheet are connected with third junctions extending in the longitudinal direction at predetermined intervals in the width direction and fourth junctions extending in the width direction at predetermined intervals in the longitudinal direction when viewed in plan, the third junctions are arranged to opposite sections of opening sections of the outer absorbent pad, and the opening sections are layered on the third junctions when viewed in plan.

According to the first aspect, it is possible to efficiently diffuse the excess liquid excretions to the outer absorbent pad when the liquid excretions are not being absorbed by the inner absorbent pad and are reaching to the intersections through the opening sections formed at the intersections indented toward the non-body side during the liquid excretion absorption because of the formation of the inner absorbent pad with absorbent polymer particles absorbing the liquid excretions that are provided in a liquid-permeable first front sheet, in a liquid-permeable first rear sheet and in between the liquid-permeable first front sheet and the liquid-permeable first rear sheet, the connections of the first front sheet and the first rear sheet with first junctions extending in the longitudinal direction at predetermined intervals in the width direction and second junctions extending in the width direction at predetermined intervals in the longitudinal direction when viewed in plan, the packing of the absorbent polymer particles within cells defined by an adjacent pair of the first junctions and an adjacent pair of the second junctions, and the formation of opening sections at intersections where the first junctions and second junctions intersect.

According to the second aspect, in addition to the effect of the first aspect and as in the embodiment of the first aspect, it is possible to have higher diffusibility of the liquid excretions toward the longitudinal direction of the center of the inner absorbent pad positioned in the crotch part of the wearer because of the formation of the opening sections formed at the center in the longitudinal direction of the inner absorbent pad made smaller than the opening sections formed in the front and rear sides in the longitudinal direction of the inner absorbent pad.

According to the third aspect, in addition to the effects of the first aspect or the second aspect, it is possible to efficiently diffuse the excess liquid excretions to the outer absorbent pad when the liquid excretions are reaching to the intersections because of the formation of the opening sections in the rectangle configurations and the arrangement of the long sides of the rectangles along with the first junctions when viewed in plan.

According to the fourth aspect, in addition to the effect of the third aspect, it is possible to efficiently diffuse the excess liquid excretions to the outer absorbent pad when the liquid excretions are reaching to the intersections because of the formation of the dimension of the long side of the rectangles made longer than the width in the longitudinal direction of the second junctions when viewed in plan. In addition to the diffuse efficiency of the excess liquid excretions to the outer absorbent pad when the liquid excretions is reaching to the intersections through the first junctions, it is possible to prevent the leakage of the excess liquid excretions toward the width direction.

According to the fifth aspect, in addition to the effects of any one of the first, second, third or fourth aspect, it is possible to quickly diffuse the excess liquid excretions to the outer absorbent pad in the longitudinal direction by the high density fiber area when the liquid excretions are transferred to the outer absorbent pad through the opening sections of the inner absorbent pad because of the formation of the outer absorbent pad with the absorbent polymer particles absorbing the liquid excretions and being placed in the liquid-permeable third front sheet, the liquid-permeable or liquid-impermeable third rear sheet and between the third front sheet and the third rear sheet, when viewed in plan, the connections of the third front sheet and the third rear sheet with third junctions extending in the longitudinal direction at predetermined intervals in the width direction and fourth junctions extending in the width direction at predetermined intervals in the longitudinal direction, the arrangement of the third junctions to the opposite sections of the opening sections of the outer absorbent pad and when viewed in plan, the arrangement of the opening sections layered on the third junctions.

According to the sixth aspect, in addition to the effects of any one of the first, second, third or fourth aspect, it is possible to quickly diffuse the excess liquid excretions to the outer absorbent pad in the longitudinal direction by the third junctions when the liquid excretions are transferred to the outer absorbent pad through the opening sections of the inner absorbent pad because of the formation of the outer absorbent pad with the absorbent polymer particles absorbing the liquid excretions and being placed in the liquid-permeable third front sheet, the liquid-permeable or liquid-impermeable third rear sheet and between the third front sheet and the third rear Sheet, the connections of the third front sheet and the third rear sheet with third junctions extending in the longitudinal direction at predetermined intervals in the width direction and fourth junctions extending in the width direction at predetermined intervals in the longitudinal direction when viewed in plan, the arrangement of the third junctions to the opposite sections of the opening sections of the outer absorbent pad and in the plan view, the arrangement of the opening sections layered on the third junctions

DETAILED DESCRIPTION

<Disposable Diapers>

The invention disclosing an absorbent pad with the excellent fluids diffusion and the excellent liquid permeability is described while referring to the figures. As used herein, the term "the longitudinal direction" refers to the direction connecting the stomach side and the back side, the term "the width direction" refers to the direction perpendicular to the longitudinal direction, the term "vertical direction" refers to the direction perpendicular to the waistline direction of disposable diapers in a worn state, the term "inner surface" refers to the body side of each component respectively, and the term "outer surface" refers to the opposite of the body side of each component respectively.

Figure 1:
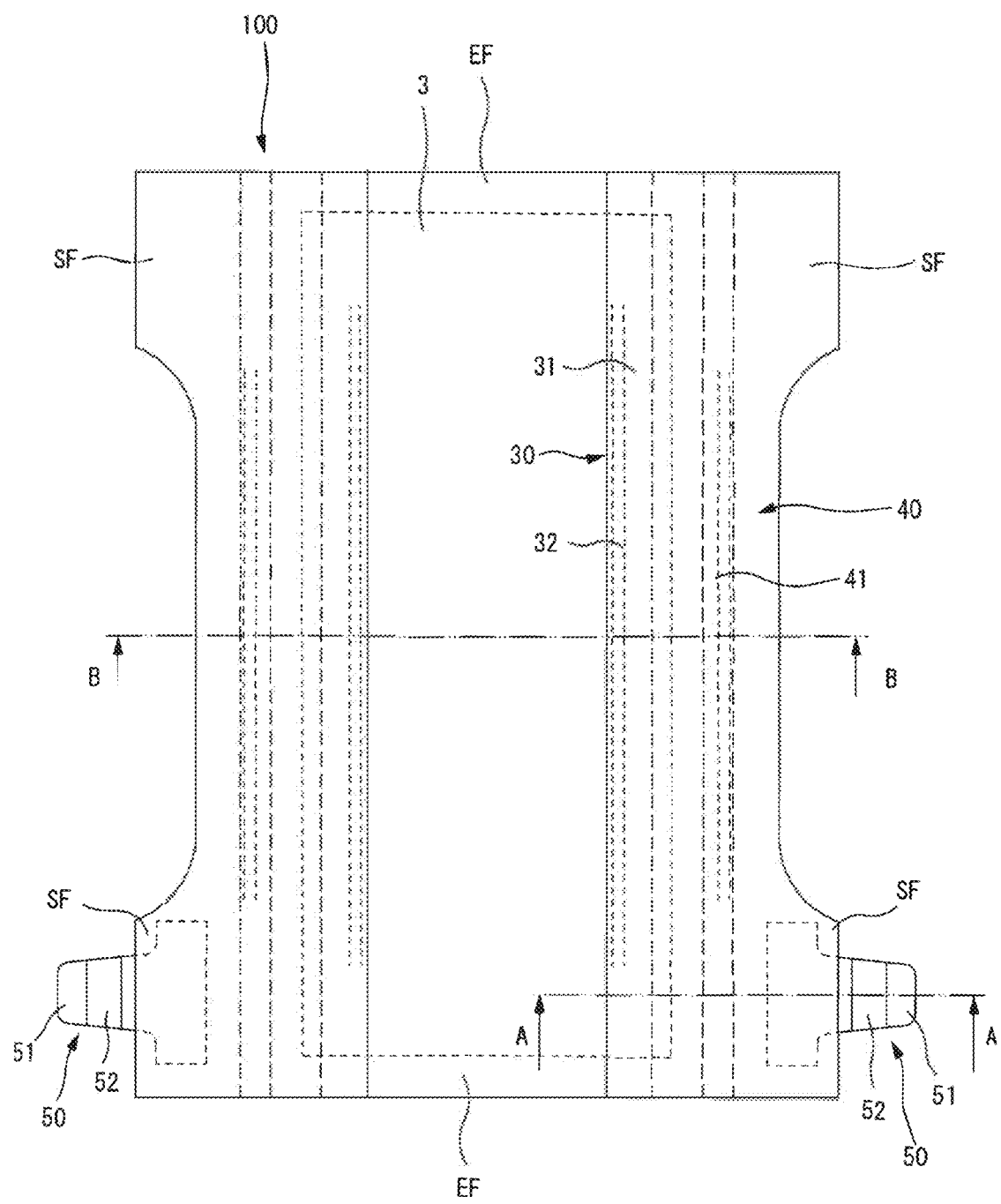
FIG. 1 is an expansion diagram showing the inner surface plan view of the disposable diapers.
Figure 2:
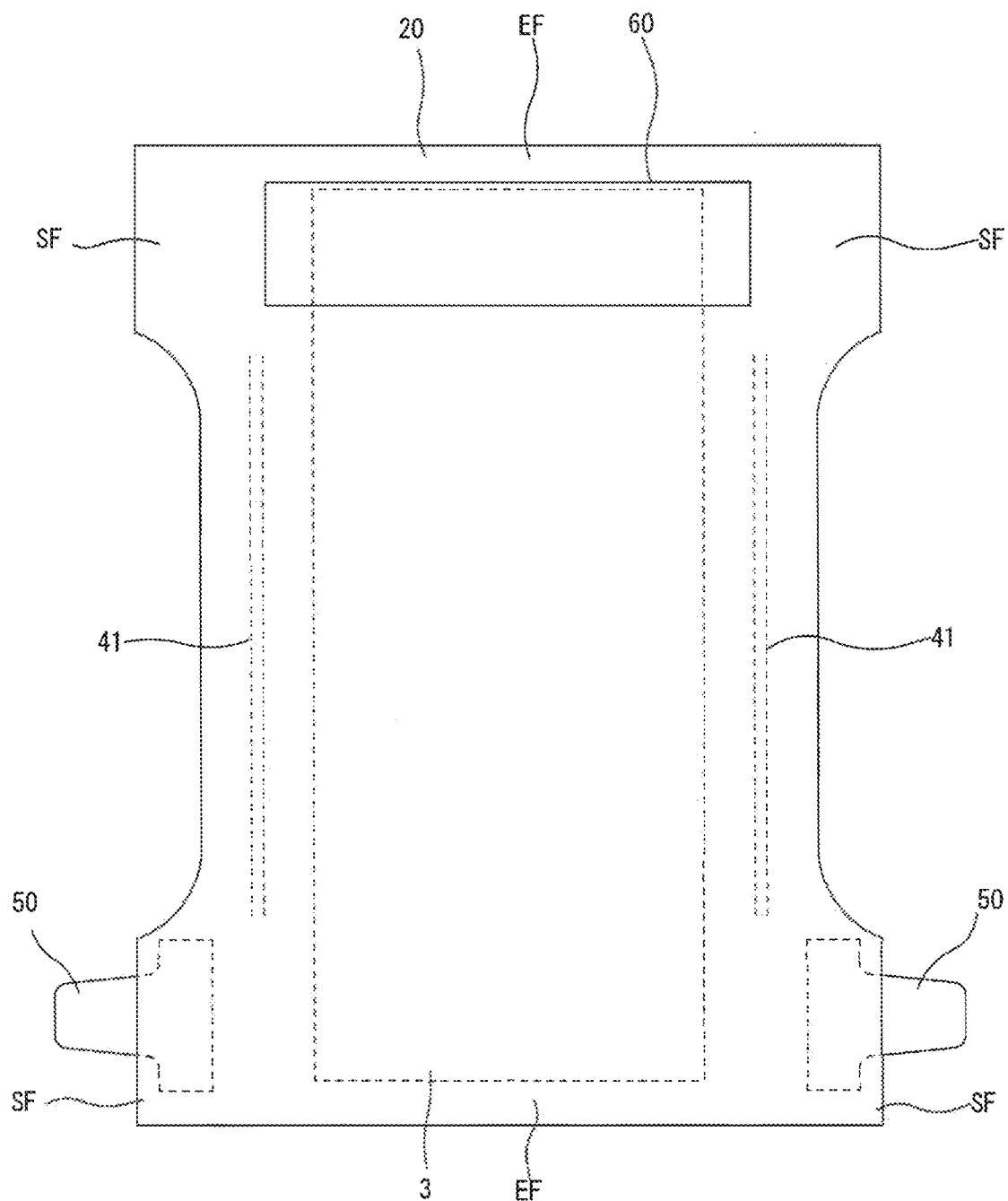
FIG. 2 is an expansion diagram showing the outer surface plan view of the disposable diapers.

As shown in FIGS. 1 and 2, the disposable diaper 100 comprises a liquid-permeable top sheet 1 on the body side, a liquid-impermeable back sheet 2 on the opposite of the body side and the absorbent pad 3 located in between the top sheet 1 and the back sheet 2. Further, an exterior sheet 20 is used for the outer surface of the back sheet 2.

The three-dimensional gather 30 for the leg circumference is used for the outside of the absorbent pad 3 in the width direction respectively to prevent the leakage of the liquid excretions to outside, and the flat gather 40 for the leg circumference preventing the leakage of the liquid excretions to outside is used for the outside of the three-dimensional gather 30 respectively.

End flaps EF, where the absorbent pad 3 does not extend, is used for the outside of the absorbent pad 3 in the longitudinal direction respectively, and side flaps SF, where the absorbent pad 3 does not extend, is used for the outside of the absorbent pad 3 in the width direction respectively.

The fastening tapes 50 extending outward in the width direction is used for the back of the side flaps part SF respectively, and a target sheet 60 locking the fastening tapes 50 when wearing the disposable diaper 100 is used for the stomach side of the outer surface of the exterior sheet 20.

(Top Sheet)

The top sheet 1 extends more outward than the peripheral line of the absorbent pad 3, and the outer surface of the extending part is fixed to the inner surface of the back sheet 2 through an adhesive agent such as a hot melt.

Porous or nonporous non-woven fabric or perforated plastic sheet may be used for the top sheet 1. For the material fibers constituting the non-woven fabric, olefins such as polyethylene or polypropylene, polyesters, synthetic fibers such as amide-based, and others including regenerated fibers such as rayon or cupra as well as natural fibers such as cotton may be used. Further, as for the methods of non-woven fabric processes, the known methods such as a spun lace method, a spun bond method, a SMS method, a thermal bond method, a melt-blown method, a needle punching method, an air-through method, and a point bond method may be used. A fiber base weight of the non-woven fabric used for the top sheet 1 is preferably 15 to 30 g/m² and the thickness is preferably 0.05 to 1 mm.

(Back Sheet)

The back sheet 2 extends more outward than the peripheral line of the absorbent pad 3 and blocks the movement of the liquid excretions absorbed to the absorbent pad 3 to outside.

The back sheet 2, in addition to plastic films such as polyethylene films, may be moisture permeable sheets while keeping the water impermeable property from the viewpoint of the stuffiness prevention may be used. Microporous sheets obtained by stretching toward the uniaxial or biaxial direction after forming the sheets by melting and kneading inorganic fillers in olefin-based resins such as polyethylene or polypropylene may be used for the sheets with the water barrier property and the moisture permeability, for example. A base weight per unit area of the back sheet 2 is preferably 13 to 40 g/m² and the thickness is preferably 0.01 to 0.1 mm.

(Absorbent Pad)

Figure 3:
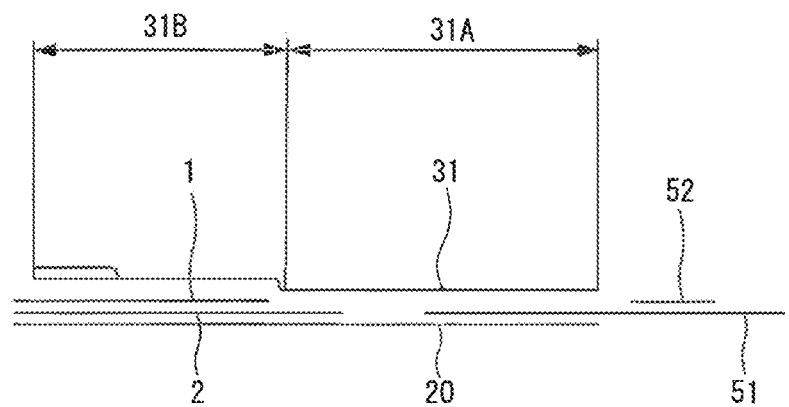
FIG. 3 is a cross sectional diagram showing A-A in FIG. 1.
Figure 4:
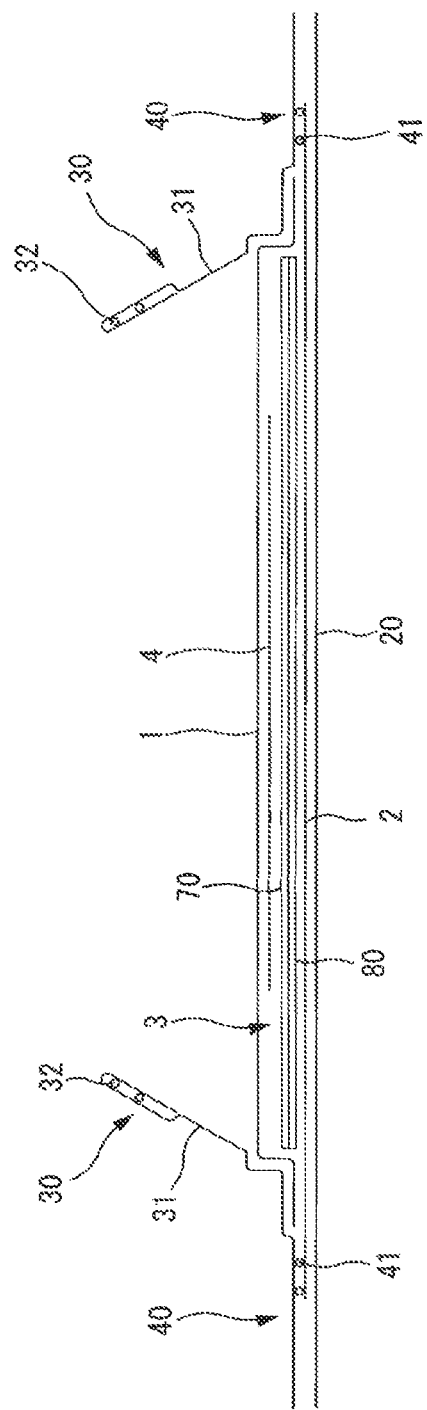
FIG. 4 is a cross sectional diagram showing B-B in FIG. 1.

As shown in FIGS. 3 and 4, the absorbent pad 3 is formed by layering the Inner absorbent pad 70 provided to the body side with the outer absorbent pad 80 provided to the non-body side. The inner absorbent pad 70 and the outer absorbent pad 80 will be described later.

(Exterior Sheet)

The exterior sheet 20 is a sheet that covers the outer surface of the back sheet 2 and has a fabric-like appearance and texture for the outer surface of the disposable diaper 100. The exterior sheet is preferably formed with non-woven fabric. As for the material fibers, olefins such as polyethylene or polypropylene, polyesters, synthetic fibers such as amide-based, and others including regenerated fibers such as rayon or cupra as well as natural fibers such as cotton may be used and as for the processes, the methods such as a spun lace method, a spun bond method, a thermal bond method, an air-through method and a needle punching method may be used for the production. However, in the viewpoint of establishing compatibility between texture and strength, long fiber non-woven fabric such as spun bond non-woven fabric, SMS non-woven fabric or SMMS non-woven fabric is preferred.

In addition to the use of non-woven fabric in one piece, it is possible to use overlapping multiple sheets, and fixing the non-woven fabric by applying an adhesive agent such as a hot melt is preferred when using overlapping multiple sheets. Further, the fiber base weight is preferably 10 to 50 g/m², especially 15 to 30 g/m² is preferred when using a non-woven fabric.

(Three-Dimensional Gather for the Leg Circumference)

The outer surface of a base 31A of the gather sheet 31 forming the three-dimensional gather 30 for the leg circumference is fixed to the outside of the inner part of the back sheet 2 in the width direction and the outside of the inner part of the exterior sheet 20 in the width direction respectively throughout the longitudinal direction. Further, the both ends of raised portions 31B of the gather sheet 31 in the longitudinal direction are fixed to the outside of the inner part of the top sheet 1 in the width direction, and the middle part of the raised portions 31B of the gather sheet 31 in the longitudinal direction is not fixed to the inner part of the top sheet 1 but separated.

The plurality of elongated elastic stretchable strips 32 with the predetermined extension shape extending in the longitudinal direction at the predetermined intervals in the width direction are provided to the raised portions 31B of the gather sheet 31. Accordingly, when wearing the disposable diaper 100, the raised portions 31B is raised toward the crotch part of the wearer by the shrinkage force of the elastic stretchable strips 32, and the leakage of the liquid excretions to outside can be prevented by pressing and contacting the tip of the raised portions 31 against the crotch part of the wearer.

The gather sheet 31, in addition to the non-woven fabric such as spun bond non-woven fabric, may be the plastic films similar to the ones used for the back sheet 2 and those laminated sheets may be used, however, in the viewpoint of establishing the feeling of the skin, non-woven fabric performed water repellent treatment is preferred.

For the elastic stretchable strips 32, regular materials such as thread-like, string-like and belt-like natural rubbers or synthetic rubbers, specifically styrene-based rubbers, olefin rubbers, urethane rubbers, ester-based rubbers, polyurethanes, polyethylenes, polystyrenes, styrene-butadienes, silicons and polyesters may be used. Further, the thickness of the elastic stretchable strips 32 is approximately 500 to 1500 dtex, especially around 800 to 1300 dtex (in case of natural rubbers, approximately 0.1 to 3 mm, especially around 0.5 to 3 mm) is preferred, and the elongation percentage at the time of installation is approximately 150 to 250%, especially around 160 to 200% is preferred.

(Flat Gather for the Leg Circumference)

The flat gather 40 for the leg circumference is provided to the base 31A of the gather sheet 31 forming the three-dimensional gather 30. The elongated elastic stretchable strips 41 with the predetermined extension shape extending in the longitudinal direction at the predetermined intervals in the width direction are provided to the base 31A of the gather sheet 31 forming the side flaps part SF and the outside of the back sheet 2 in the width direction. Accordingly, when wearing the disposable diaper 100, the flat gather 40 is pressing and contacting to the crotch part of the wearer by the shrinkage force of the elastic stretchable strips 41, and the leakage of the liquid excretions to outside can be prevented.

For the elastic stretchable strips 41, regular materials such as thread-like, string-like and belt-like natural rubbers or synthetic rubbers, specifically styrene-based rubbers, olefin rubbers, urethane rubbers, ester-based rubbers, polyurethanes, polyethylenes, polystyrenes, styrene-butadienes, silicons and polyesters may be used. In addition, the spacing between the elastic stretchable strips 41 is approximately 2 to 15 mm, especially around 3 to 7 mm is preferred. Further, the thickness of the elastic stretchable strips 41 is approximately 500 to 1500 dtex, especially around 800 to 1300 dtex (in case of natural rubbers, approximately 0.1 to 3 mm, especially around 0.5 to 3 mm) is preferred, and the elongation percentage at the time of installation is approximately 150 to 250%, especially around 160 to 200% is preferred.

(Fastening Tapes)

As shown in FIGS. 1 to 3, the fastening tapes 50 extending toward outside is provided to the back of the side flaps part SF respectively. The fastening tapes 50 comprises the base sheet 51 and the locking section 52 provided to the outside of the inner surface of the base sheet 51. Further, the inner part of the base sheet 51 is fixed to the outside of the gather sheet 31 and the exterior sheet 20 in the width direction.

The non-woven fabric is preferred for the material of the base sheet 51 and any known non-woven fabric may be used without a particular limitation. For the material fibers constituting the non-woven fabric, olefins such as polyethylene or polypropylene, polyesters, synthetic fibers such as amide-based, and others including regenerated fibers such as rayon or cupra as well as natural fibers such as cotton may be used. Further, for the methods of non-woven fabric processes, the known methods such as a spun lace method, a spun bond method, a SMS method, a thermal bond method, a melt-blown method, a needle punching method, an air-through method, and a point bond method may be used. Especially, the spun bond non-woven fabric using olefin fibers and SMS non-woven fabric are preferred. Although the base weight of the non-woven fabric used may be appropriately determined, the total base weight of the non-woven fabric for the main unit 5b is 20 to 75 g/m$^2$, especially 26 to 46 g/m$^2$, and the total base weight of the non-woven fabric for the fixed part 5f and the tip part 5p is 35 to 130 g/m$^2$ respectively, especially 46 to 116 g/m$^2$, are preferred. Within this range, it is possible to ensure the strength and the rigidity of the base section fixed in between the exterior sheet 20 and the gather sheet 31, and further secure the flexibility and the elasticity of the main unit 74.

For the locking section 52, hook materials of a mechanical fastener are preferred. The hook materials may have multiple engaging protrusions. The configuration of the engaging protrusions may be in shapes such as (A) a mirror-inverted J shape, (B) J-shape, (C) mushroom-shape, (D) T-shape and (E) a dual J shape (a combination of two Js joined together back to back like a fishhook), but it may be in any shape. Alternatively, it is possible to use pressure-sensitive adhesive layers instead of the hook materials.

(Target Sheet)

For the target sheet 60, preferred materials are such as plastic films with plurality of loop yarn on the surface side and non-woven fabrics. Thus, when wearers wear the disposable diaper 100, it is possible to efficiently lock the locking section 52 of the fastening tapes 50 to the target sheet 60.

(Interlayer Sheet)

In the first embodiment, the interlayer sheet 4 is provided in between the top sheet 1 and the absorbent pad 3. Thus, the liquid excretions passing through the top sheet 1 can move quickly to the absorbent pad 3 and it is possible to prevent the liquid excretions from returning to the top sheet 1. It is noted that the interlayer sheet 4 is fixed to the outside of the top sheet 1 by a hot melt adhesive agent, heat embossing or ultrasonic wave welding.

For the interlayer sheet 4, in addition to the use of the non-woven fabrics, resin films with numerous permeation holes may be used. For the non-woven fabrics, the materials similar to the top sheet 1 may be used, however, the materials having higher hydrophilicity and fiber density than the top sheet 1 is preferred in order to have excellent movement properties of the liquid excretions from the top sheet 1 to the interlayer sheet 4.

<Inner Absorbent Pad>

First Embodiment

Figure 5:
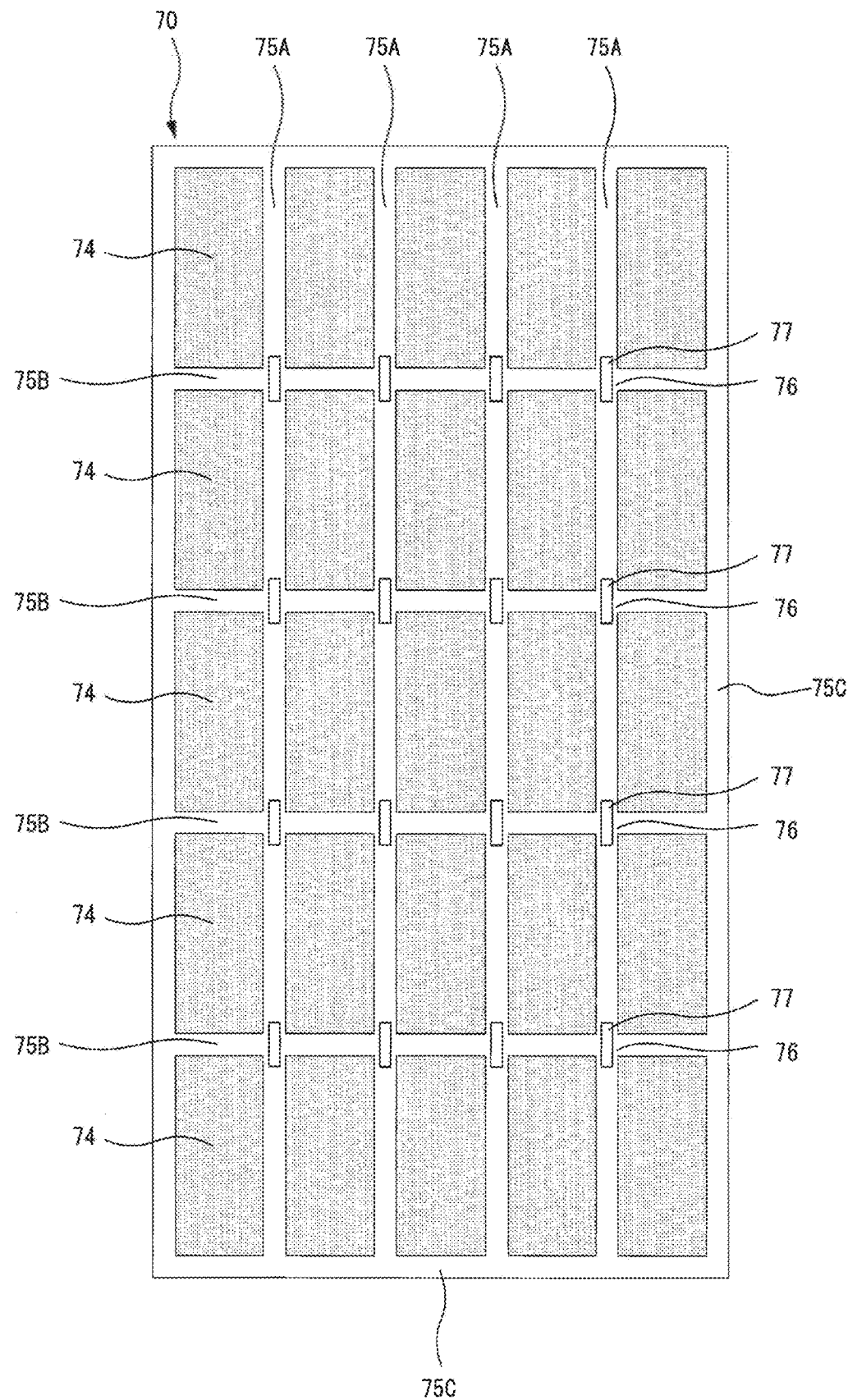
FIG. 5 is a diagram showing the inner surface plan view of the inner absorbent pad of the first embodiment.
Figure 10:
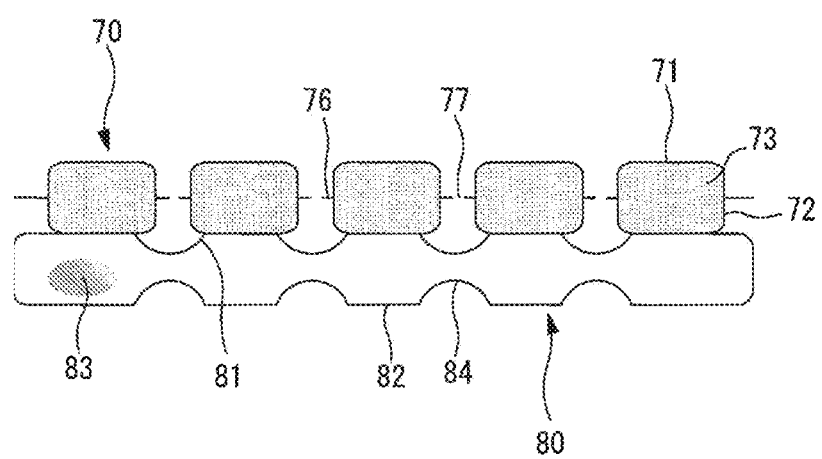
FIG. 10 is a cross sectional diagram showing A-A in FIG. 9.
Figure 11:
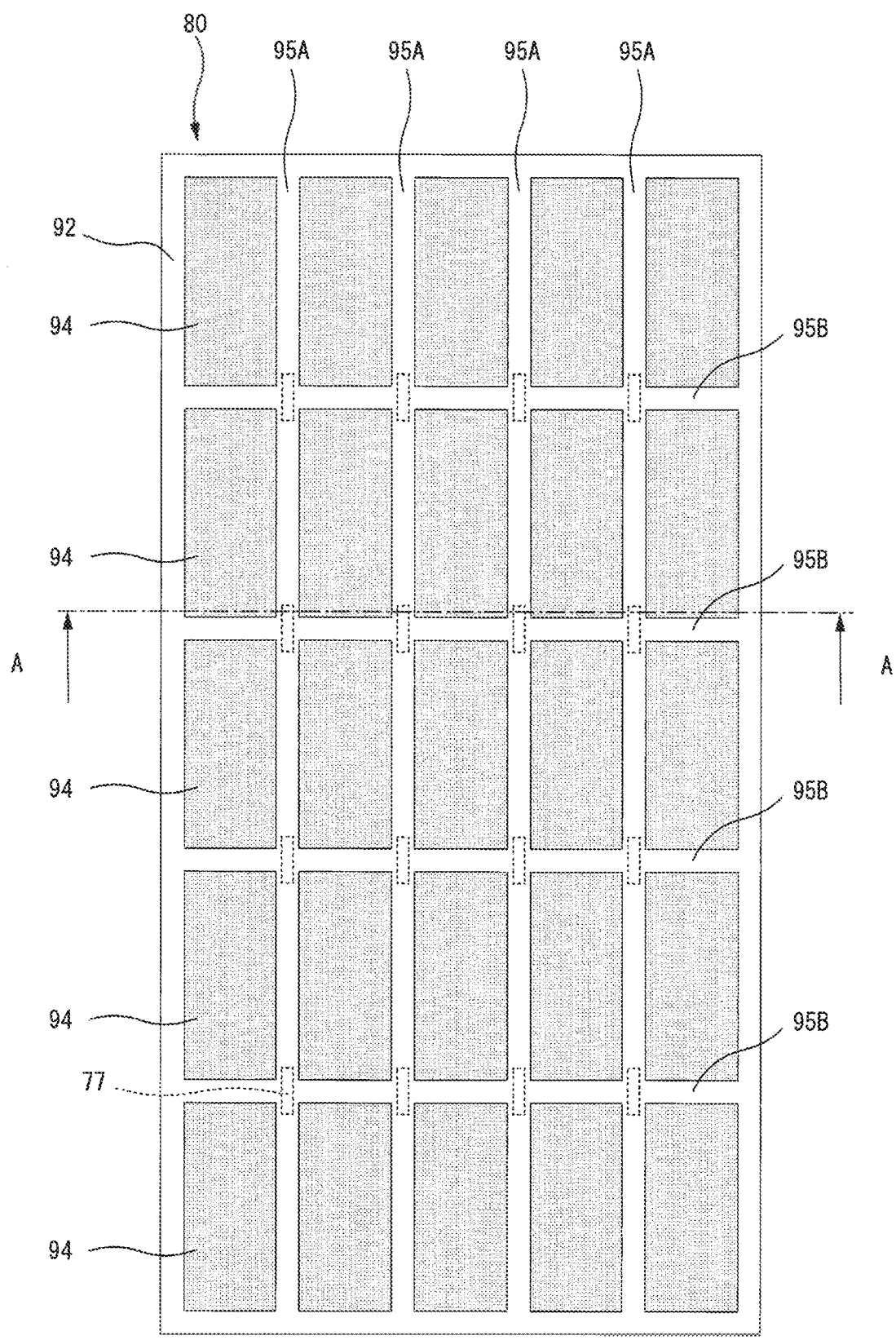
FIG. 11 is a diagram showing the outer surface plan view of the outer absorbent pad of the second embodiment provided to the outside of the inner absorbent pad of the first embodiment.

The inner absorbent pad 70 in the first embodiment provided to the body side of the absorbent pad 3 is described herein. As shown in FIGS. 5, 10 and 11, the inner absorbent pad 70 is formed with the absorbent polymer particles 73 provided in the liquid-permeable front sheet 71 ("First front sheet" recited in claims) on the body side, in a liquid-permeable rear sheet 72 ("First rear sheet" recited in claims) on the non-body side and in between the front sheet 71 and the rear sheet 72.

The front sheet 71 and the rear sheet 72 are connected by the junctions. The absorbent polymer particles 73 are used for plurality of the cells 74 in the rectangle configurations having a long side in the longitudinal direction laid out by the junctions respectively. It is noted that the front sheet 71 and the rear sheet 72 positioned to the cells 74 are separated without connections and formed with predetermined spaces. Thus, it is possible to prevent the absorbent polymer particles 73 from being in one part of the inner absorbent pad 70 and the absorption performance of the inner absorbent pad 70 can be maintained. Further, in addition to being able to unbind the absorbent polymer particles 73 for the front sheet 71 or the rear sheet 72, it is possible to bond to the front sheet 71 or the rear sheet 72 by using a hot melt adhesive agent. Therefore, essentially cutter blade spillage of cutting machines can be prevented resulting in the enhancement of the productivity.

The junctions are formed with 4 of the junctions 75A ("First junctions" recited in claims) extending toward the longitudinal direction at the predetermined intervals in the width direction of the inner absorbent pad 70, 4 of the junctions 75B ("Second junctions" recited in claims) extending toward the width direction at the predetermined intervals in the longitudinal direction of the inner absorbent pad 70 and the junctions 75C extending to the outer peripheral part of the inner absorbent pad 70. Further, the cells 74 laid out by the Junctions 75A, the junctions 75B and the junctions 75C are formed into 5 sections at the predetermined intervals in the width direction and into 5 sections at the predetermined intervals in the longitudinal direction creating the total of 25 cells 74. It is noted that, in the first embodiment, the numbers of the junctions 75A and the junctions 75B may be set arbitrarily.

The opening sections 77 having the long side in the longitudinal direction are provided respectively to the intersections 76 where the junctions 75A and the junctions 75B intersect. Therefore, when the cells 75 are swelled by absorbing the liquid excretions, plenty of liquid excretions (hereinafter referred to the excess liquid excretions) not being absorbed by the cells 76 result in flowing into the Intersections 76 being at the lowest position (positioned on the non-body side) with respect to the junctions 75A and the junctions 75B, and it is possible to transfer most of the flowed excess liquid excretions to the outer absorbent pad 80 through the opening sections 77.

Similar to the top sheet 1, porous or nonporous non-woven fabric or perforated plastic sheet may be used for the front sheet 71. When using a non-woven fabric, use of a high fiber density non-woven fabric produced by a spun bond method, a melt-blown method or a needle punching method is preferred, and in addition, when using a plastic sheet, use of a plastic sheet formed with smaller diameter holes than the outer diameter of the absorbent polymer particles 73 is preferred. Therefore, it is possible to minimize the escape of the absorbent polymer particles 73 from the cells 74.

Similar to the top sheet 1, porous or nonporous non-woven fabric or perforated plastic sheet may be used for the rear sheet 72. Further, when using a non-woven fabric, use of a high fiber density non-woven fabric produced by a spun bond method, a melt-blown method or a needle punching method is preferred, and in addition, when using a plastic sheet, use of a plastic sheet formed with smaller diameter holes than the outer diameter of the absorbent polymer particles 73 is preferred. Therefore, it is possible to minimize the escape of the absorbent polymer particles 73 from the cells 74.

The high absorbent polymer particles used for absorption items such as disposable diapers and sanitary napkins may be used for the absorbent polymer particles 73. The high absorbent polymer particles may be starch, cellulose and synthetic polymers, and starch-acrylic acid (salt) graft copolymer, saponified product of starch—acrylonitrile copolymer, crosslinked products of sodium carboxymethylcellulose and acrylic acid (salt) polymer.

The water absorption of the absorbent polymer particles 73 is preferably more than 40 g/g and the water absorption rate is preferably less than 70 seconds, especially less than 40 seconds. Accordingly, it is possible to efficiently absorb the liquid excretions passing through the top sheet 1 with the inner absorbent pad 70 and to prevent the liquid excretions from returning to the top sheet 1.

The gel strength of the absorbent polymer particles 73 is preferably more than 1,000 Pa. Accordingly, it is possible to reduce the stickiness of the inner absorbent pad 70 absorbing the liquid excretions.

The particle diameter of the absorbent polymer particles 73 is preferably, when sifting (shaking for 5 minutes) by using a 500 μm standard sieve (JISZ8801—1:2006) and sifting (shaking for 5 minutes) the particles falling under the sieve with the sifting by using a 180 μm standard sieve (JISZ8801—1:2006), such that the ratio of the particles remaining on the 500 μm standard sieve is less than 30 wt. % and the ratio of the particles remaining on the 180 μm standard sieve is more than 60 wt. %.

The fiber base weight of the absorbent polymer particles 73 of the cells 74A, although determined appropriately depending on the absorption amount required, is preferably 50 to 350 $g/m^2$. Further, ensuring the absorption amount becomes difficult if the fiber base weight is less than 50 $g/m^2$ and the absorption amount becomes too excessive if the fiber base weight is more than 350 $g/m^2$. In addition, the configuration of the cells 74 is formed in rectangles when viewed in plan, however, shapes of square, rhombus, hexagon, circle, and ellipse can be formed as well. Furthermore, when the cells 74 is hexagonal shapes, the junctions 75 extend in the longitudinal direction as they form  in the width direction along the shapes of hexagons in the width direction, and similarly, the junctions 76 extend in the width direction as they form  in the longitudinal direction along the shapes of hexagons in the longitudinal direction.

The width in the width direction of the junctions 75A extending in the longitudinal direction is formed in 5 to 10 mm, the width in the longitudinal direction of the junctions 75B extending in the width direction is formed in the 5 to 10 mm and the width in the width direction and the longitudinal direction of the junctions 75C extending to the outer peripheral part of the inner absorbent pad 70 is formed in 5 to 10 mm. Therefore, the liquid excretions passing through the top sheet 1 can be spread throughout the entire inner absorbent pad 70 and the liquid excretions can be absorbed efficiently with the plurality of cells 74.

The junctions 75A, the junctions 75B and the junctions 75C are preferably bonded by welding the front sheet 71 and the rear sheet 72 similar to ultrasonic wave welding or heat sealing, however, a hot melt adhesive agent may be used for bonding.

The dimension in the longitudinal direction of the opening sections 77 is preferably 100 to 200% with respect to the width of the up-and-down direction of the junctions 75B. There is a possibility of the excess liquid excretions flowed into the intersections 76 may remain near the intersections 76 if the dimension in the longitudinal direction of the opening sections 77 is less than 100%, and there is a risk of breakage of the cells 74 if it is over 200% due to the reduction of the joint strength of the junctions 75A. It is noted that the dimension in the longitudinal direction of the opening sections 77 shown in FIG. 5 is formed 170% with respect to the width in the up-and-down direction of the junctions 75B.

The width in the width direction of the opening sections 77 is preferably 10 to 90% with respect to the width in the width direction of the junctions 75A. There is a possibility of the excess liquid excretions flowed into the intersections 76 may remain near the intersections 76 if the width in the width direction of the opening sections 77 is less than 10%, and there is a risk of breakage of the cells 74 if it is over 90% due to the reduction of the joint strength of the junctions 75A. It is noted that the width in the width direction of the opening sections 77 shown in FIG. 5 is formed 50% with respect to the width in the width direction of the junctions 75A. In addition, the opening sections 77 may be formed in ellipse configurations having the long diameter in the longitudinal direction, hourglass configurations having the long side in the longitudinal direction or cross configurations extending in the longitudinal direction and the width direction.

Second Embodiment

Figure 6:
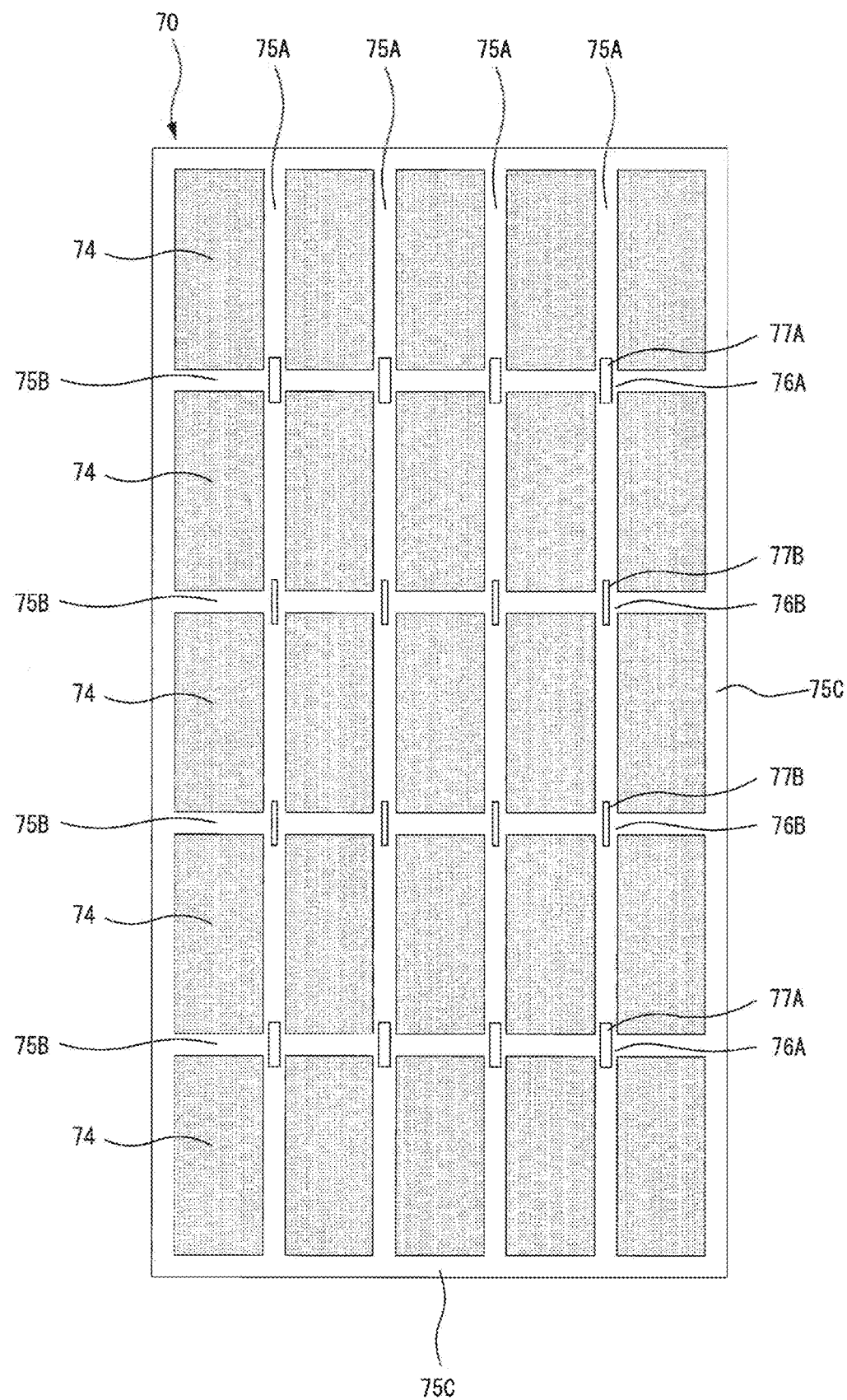
FIG. 6 is a diagram showing the inner surface plan view of the inner absorbent pad of the second embodiment.

Next, the inner absorbent pad 70 of the second embodiment is described. It is noted that the same components as the inner absorbent pad 70 in the first embodiment are described with the same reference numerals and the explanations are not repeated. As shown in FIG. 6, the opening sections 77A having the long side in the longitudinal direction are provided respectively to the Intersections 76A where the junctions 75A and one junction 75B provided in the front part of the upper absorbent pad 70 in the longitudinal direction and one junction 75B provided in the rear part of the upper absorbent pad 70 in the longitudinal direction intersect. Further, the opening sections 77A are formed in the same configurations as the opening sections 77.

The opening sections 77B having the long side in the longitudinal direction are provided respectively to the intersections 76B where the junctions 75A and one Joint 75B provided to the shifted section of the front of the center of the upper absorbent pad 70 in the longitudinal direction and one Joint 75B provided to the shifted section of the rear of the center of the upper absorbent pad 70 in the longitudinal direction intersect. It is noted that the opening sections 77B are formed smaller than the opening sections 77A. Therefore, the liquid excretions transferred to the center part of the upper absorbent pad 70 in the longitudinal direction and the width direction through the top sheet 1 may be diffused quickly toward the outer peripheral part of the inner absorbent pad 70 by the junctions 75A extending toward the longitudinal direction and the junctions 75B extending toward the width direction of the inner absorbent pad 70, and in addition, it is possible to further prevent the liquid excretions from returning to the top sheet 1.

The dimension in the longitudinal direction of the opening sections 77B is preferably 100 to 200% with respect to the width of the up-and-down direction of the junctions 75B. There is a possibility of the excess liquid excretions flowed into the Intersections 76 may remain near the intersections 76B if the dimension in the longitudinal direction of the opening sections 77B is less than 100%, and there is a risk of breakage of the cells 74 if it is over 200% due to the reduction of the joint strength of the junctions 75A. It is noted that the dimension in the longitudinal direction of the opening sections 77B shown in FIG. 6 is formed 170% with respect to the width in the up-and-down direction of the junctions 75B.

The width in the width direction of the opening sections 77B is preferably 5 to 45% with respect to the width in the width direction of the junctions 75A. There is a possibility of the excess liquid excretions flowed into the intersections 76B may remain near the intersections 76B if the width in the width direction of the opening sections 77B is less than 5%, and there is a risk of the reduction of diffusibility of the excess liquid excretions flowed into the intersections 76B diffusing through the junctions 75A extending from the intersections 76B toward the longitudinal direction and the junctions 75B extending from the intersections 75B toward the width direction if it is over 45%. It is noted that the width in the width direction of the opening sections 77B shown in FIG. 6 is formed 25% with respect to the width in the width direction of the junctions 75A.

Third Embodiment

Figure 7:
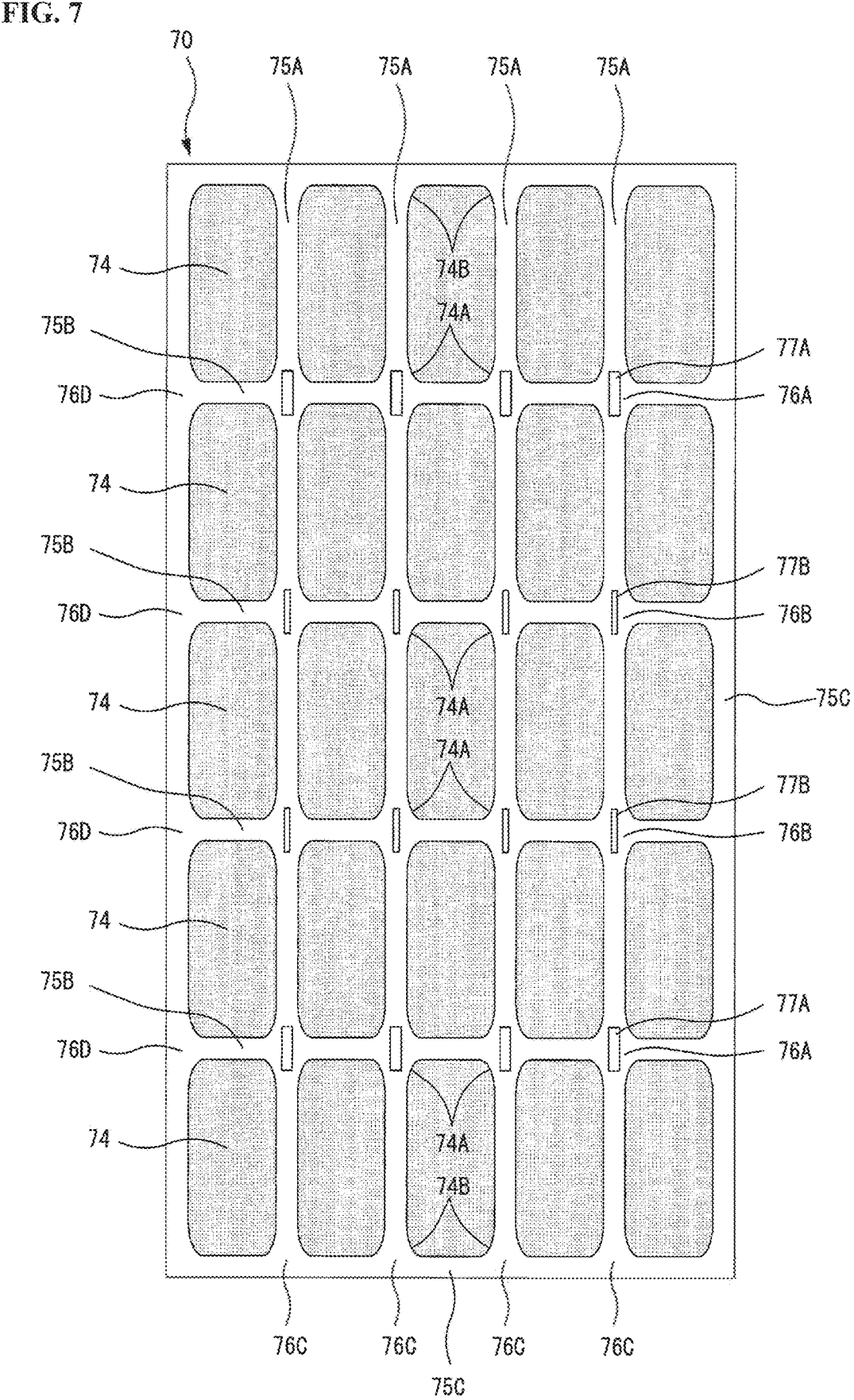
FIG. 7 is a diagram showing the inner surface plan view of the inner absorbent pad of the third embodiment.

Next, the inner absorbent pad 70 of the third embodiment is described. It is noted that the same components as the inner absorbent pad 70 in the second embodiment are described with the same reference numerals and the explanations are not repeated. As shown FIG. 7, the corners 74A of the cells 74 opposite to the Intersections 76A where the junctions 75A and one Joint 75B provided in the front part of the upper absorbent pad 70 in the longitudinal direction and one Joint 75B provided in the rear part of the upper absorbent pad 70 in the longitudinal direction intersect are formed in circular configurations having predetermined radius. Further, the corners 74A of the cells 74 opposite to the intersections 76B where junctions 75A and one Joint 75B provided to the shifted section of the front of the center of the upper absorbent pad 70 in the longitudinal direction and one junction 75B provided to the shifted section of the rear of the center of the upper absorbent pad 70 in the longitudinal direction intersect are formed in circular configurations having predetermined radius. Therefore, the liquid excretions transferred to the center part of the upper absorbent pad 70 in the longitudinal direction and the width direction through the top sheet 1 may be diffused quickly toward the outer peripheral part of the inner absorbent pad 70 by the junctions 75A extending toward the longitudinal direction and the junctions 75B extending toward the width direction of the inner absorbent pad 70, and in addition, it is possible to further prevent the liquid excretions from returning to the top sheet 1.

Similar to the corners 74A, the corners 74B of the cells 74 opposite to the intersections 76C where the junctions 75A and the junctions 75C intersect and the intersections 76D where the junctions 75B and the junctions 75C intersect are formed in circular configurations having predetermined radius. Therefore, the inner absorbent pad 70 may be easily produced continuously.

Fourth Embodiment

Figure 8:
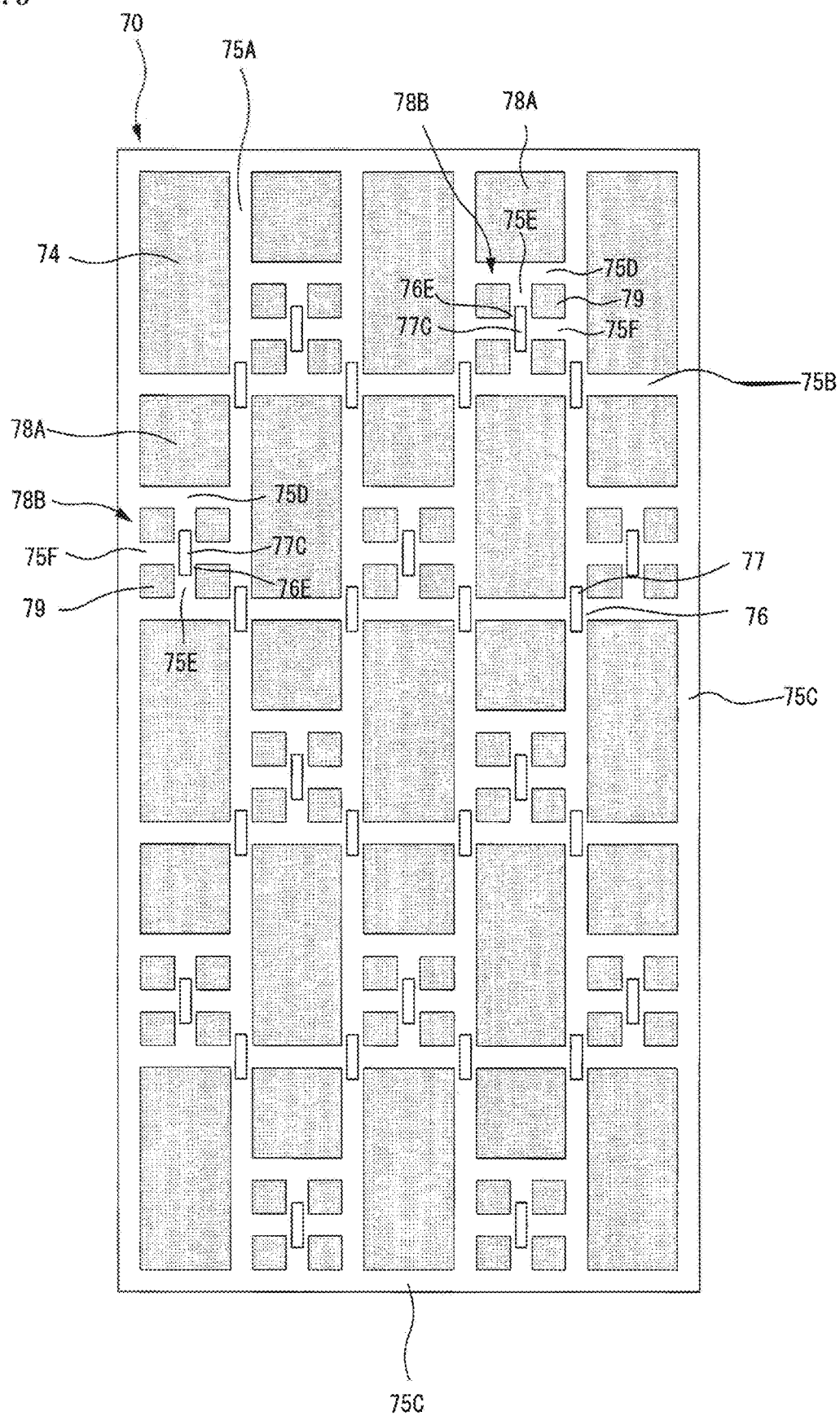
FIG. 8 is diagram showing the inner surface plan view of the inner absorbent pad of the fourth embodiment.

Next, the inner absorbent pad 70 of the fourth embodiment is described. It is noted that the same components as the inner absorbent pad 70 in the first embodiment are described with the same reference numerals and the explanations are not repeated. As shown FIG. 8, the cells 74 adjacent to the cells 74 in the longitudinal direction and the width direction are divided into the front side cells 78A in the square configurations positioned in the front side and the rear side cells 78B in the square configurations positioned in the rear side that are separated by the junctions 75D extending toward the width direction, and further, the rear side cells 78B are divided into 4 small cells 79 in the small square configurations by the junctions 75E ("First junctions" recited in claims) extending toward the longitudinal direction and the junctions 75F ("Second junctions" recited in claims) extending toward the width direction. Therefore, the heights on the body side of the ells 74, the cells 78A and the small cells 79 that have swelled by absorbing the liquid excretions may be different, and the liquid excretions transferred to the inner absorbent pad 70 through the top sheet 1 may be diffused even quicker over the entire area of the inner absorbent pad 70.

The opening sections 77C having the long side in the longitudinal direction are provided respectively to the intersections 76E where the junctions 75E and the junctions 75F intersect. Therefore, when the cells 74, the cells 78A and the small cells 79 have swelled, the excess liquid excretions flowed into the intersections 75A are transferred to the outer absorbent pad 80 through the opening sections 77 and the excess liquid excretions flowed into the intersections 76E are transferred to the outer absorbent pad 80 through the opening sections 77C.

<Outer Absorbent Pad>

First Embodiment

Figure 9:
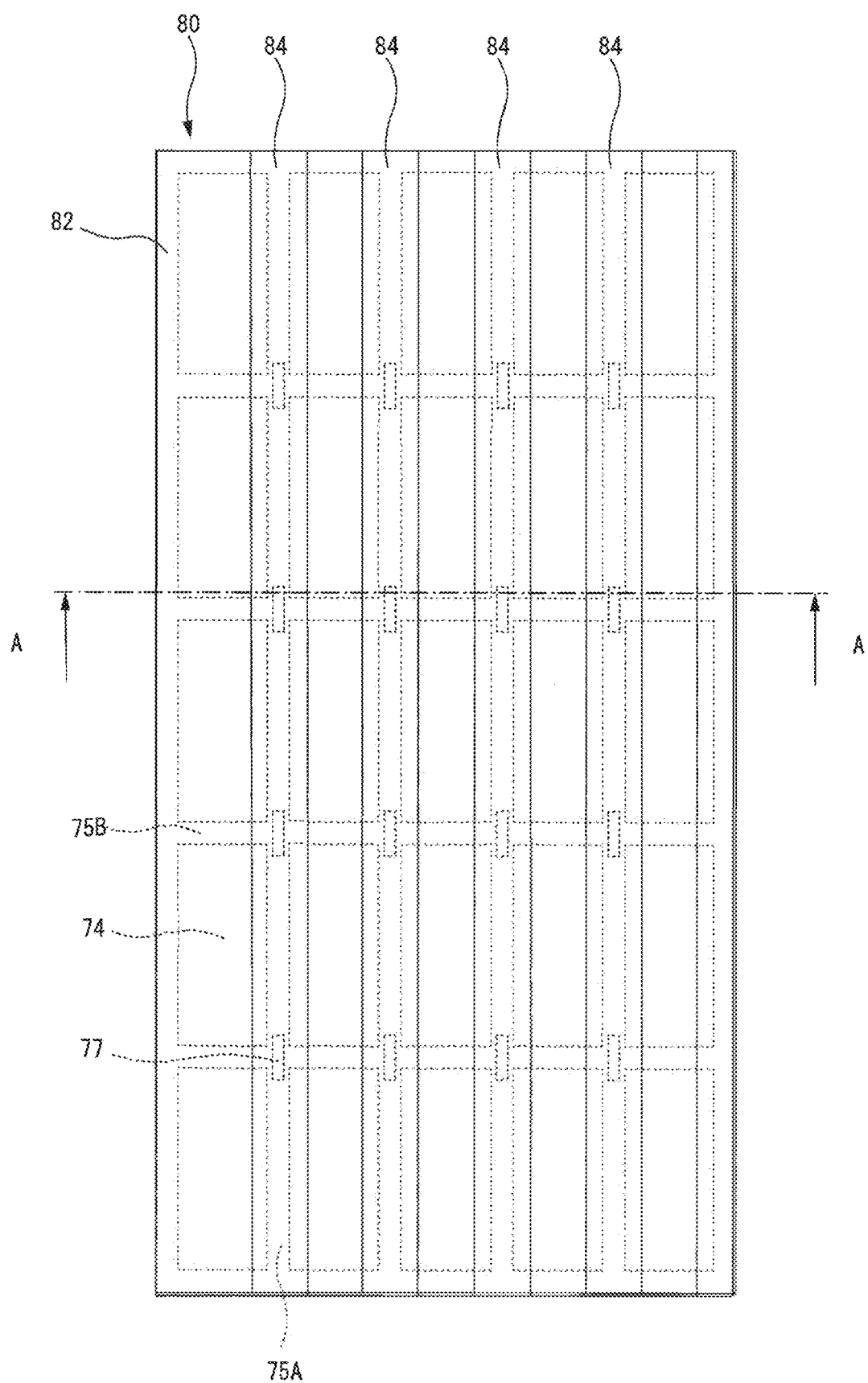
FIG. 9 is a diagram showing the outer surface plan view of the outer absorbent pad of the first embodiment provided to the outside of the inner absorbent pad of the first embodiment.

The outer absorbent pad 80 of the first embodiment provided to the non-body side of the absorbent pad 3 is described. As shown FIGS. 9 and 10, the outer absorbent pad 80 is formed with the liquid-permeable front sheet 81 ("Second front sheet" recited in claims) on the body side, the liquid-permeable rear sheet 82 ("Second rear sheet" recited in claims) on the non-body side and the absorbent core 83 provided in between the front sheet 81 and the rear sheet 82. It is noted that the dashed line in FIG. 9 shows the cells 74, the junctions 75A and 75B and the opening section 77 of the inner absorbent pad 70 layered on the inner side of the outer absorbent pad 80.

when viewed in plan, the high fiber density areas 84 such as emboss area extending toward the longitudinal direction at the predetermined intervals in the width direction are formed. In addition, when the absorbent pad 3 is formed by layering the inner absorbent pad 70 and the outer absorbent pad 80, the high fiber density areas 84 of the outer absorbent pad 80 are arranged beneath the opening section 77 of the inner absorbent pad 70. Therefore, it is possible to quickly diffuse the excess liquid excretions transferred to the outer absorbent pad 80 through the opening sections 77 of the inner absorbent pad 70 to the longitudinal direction of the outer absorbent pad 80 by the high fiber density areas 84 and to absorb the liquid excretions by the entire area of the outer absorbent pad 80, and further, it is possible to prevent the excess liquid excretions from leaking to outside.

Similar to the top sheet 1, porous or nonporous non-woven fabric or perforated plastic sheet may be used for the front sheet 81. When using a non-woven fabric, use of a high fiber density non-woven fabric produced by a spun bond method, a melt-blown method or a needle punching method is preferred.

Similar to the top sheet 1, porous or nonporous non-woven fabric or perforated plastic sheet may be used for the rear sheet 82. Moreover, when using a non-woven fabric, use of a high fiber density non-woven fabric produced by a spun bond method, a melt-blown method or a needle punching method is preferred. Further, as for the rear sheet 82, similar to the back sheet 2, in addition to plastic films such as polyethylene films, moisture permeable sheets without losing the water barrier property from the viewpoint of the stuffiness prevention may be used.

For the absorbent core 83, the use of a pulp fiber product, a filament assembly such as cellulose acetate, or non-woven fabric is as a base, a material produced by mixing or fixing high absorbent polymers may be used as needed. The pulp weight of the absorbent core 83 is preferably 100 to 500 g/m$^2$ and the thickness is preferably 1 to 15 mm. In addition, the weight of the high water absorption resin is preferably 0 to 300 g/m$^2$, it does not give enough absorption if the content of the high water absorbent resin is too small, and no entanglement between pulp fibers results in easily developing wrinkles or cracks if too large.

Second Embodiment

Figure 12:
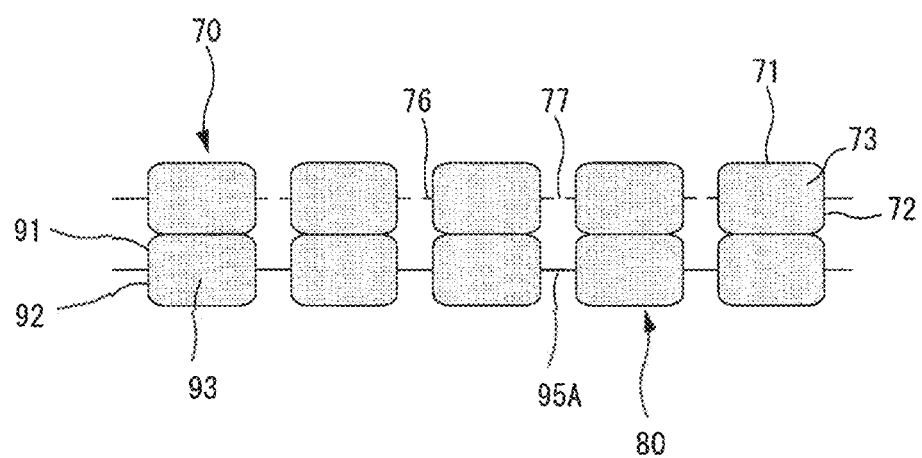
FIG. 12 is a cross sectional diagram showing A-A in FIG. 11.

The outer absorbent pad 80 of the second embodiment provided to the non-body side of the absorbent pad 3 is described. As shown FIGS. 11 and 12, the outer absorbent pad 80 is formed with the liquid-permeable front sheet 91 ("Third front sheet" recited in claims) on the body side, the liquid-permeable rear sheet 92 ("Third rear sheet" recited in claims) on the non-body side and the absorbent polymer particles 93 provided in between the front sheet 91 and the rear sheet 92. It is noted that the dashed line in FIG. 11 shows the cells 74, the opening section 77 of the inner absorbent pad 70 layered on the inner side of the outer absorbent pad 90.

The front sheet 91 and the rear sheet 92 are connected by the junctions. The absorbent polymer particles 93 are used in plurality of the cells 94 in the rectangle configurations having the long side in the longitudinal direction that are laid out by the junctions respectively.

when viewed in plan, junctions are formed with the junctions 95A ("Third junctions" recited in claims) extending toward the longitudinal direction at the predetermined intervals in the width direction and the junctions 95B ("Fourth junctions" recited in claims) extending toward the width direction at the predetermined intervals in the longitudinal direction. In addition, when the absorbent pad 3 is formed by layering the inner absorbent pad 70 and the outer absorbent pad 90, the junctions 95A extending toward the longitudinal direction of the outer absorbent pad 90 are arranged beneath the opening section 77 of the inner absorbent pad 70. Therefore, it is possible to move the excess liquid excretions transferred to the space formed in between the junctions 75A of the inner absorbent pad 70 and the junctions 95A of the outer absorbent pad 90, and it is possible to prevent the excess liquid excretions from leaking to outside.

Similar to the top sheet 1, porous or nonporous non-woven fabric or perforated plastic sheet may be used for the front sheet 91. When using a non-woven fabric, use of a high fiber density non-woven fabric produced by a spun bond method, a melt-blown method or a needle punching method is preferred, and in addition, when using a plastic sheet, use of a plastic sheet formed with smaller diameter holes than the outer diameter of the absorbent polymer particles 73 is preferred.

Similar to the top sheet 1, porous or nonporous non-woven fabric or perforated plastic sheet may be used for the rear sheet 92. Further, when using a non-woven fabric, use of a high fiber density non-woven fabric produced by a spun bond method, a melt-blown method or a needle punching method is preferred, and in addition, when using a plastic sheet, use of a plastic sheet formed with smaller diameter holes than the outer diameter of the absorbent polymer particles 73 is preferred.

The high absorbent polymer particles used for absorption items such as disposable diapers and sanitary napkins may be used for the absorbent polymer particles 93. The high absorbent polymer particles may be starch, cellulose and synthetic polymers, and starch-acrylic acid (salt) graft copolymer, saponified product of starch-acrylonitrile copolymer, crosslinked products of sodium carboxymethylcellulose and acrylic acid (salt) polymer.

INDUSTRIAL APPLICABILITY OF INVENTION

The present invention is available for absorbent articles such as tape type disposable diapers, pants type disposable diapers and sanitary napkins and pads.

The invention claimed is:

1. An absorbent pad comprising:
    an inner absorbent pad positioned on the body side is layered with an outer absorbent pad positioned on the non-body side wherein
    the inner absorbent pad is formed with a liquid-permeable first front sheet, and a liquid-permeable first rear sheet and absorbent polymer particles absorbing liquid excretions that are provided in between the liquid-permeable first front sheet and the liquid-permeable first rear sheet;
    the first front sheet and the first rear sheet are connected with first junctions extending in the longitudinal direction at predetermined intervals in the width direction and second junctions extending in the width direction at predetermined intervals in the longitudinal direction when viewed in plan;

absorbent polymer particles are packed within cells defined by an adjacent pair of the first junctions and an adjacent pair of the second junctions; and opening sections are formed at intersections where the first junctions and second junctions intersect.

2. The absorbent pad of claim 1, wherein the opening sections formed at the center in the longitudinal direction of the inner absorbent pad are made smaller than the opening sections formed in the front and rear sides in the longitudinal direction of the inner absorbent pad.

3. The absorbent pad of claim 2, wherein the opening sections are formed in the rectangle configurations and the long sides of the rectangles are provided along with the first junctions when viewed in plan.

4. The absorbent pad of claim 2, wherein:

the outer absorbent pad is formed with a liquid-permeable second front sheet, a liquid-permeable or liquid-impermeable second rear sheet and absorbent core constituting pulp fibers and absorbent polymer particles absorbing liquid excretions and being placed in between the second front sheet and the second rear sheet;

high fiber density areas are arranged with higher pulp fiber density than the adjacent sections to the opposite sites of the opening sections of the outer absorbent pad; and the opening sections are layered on the high fiber density areas when viewed in plan.

5. The absorbent pad of claim 2, wherein:

the outer absorbent pad is formed with a liquid-permeable third front sheet, a liquid-permeable or liquid-impermeable third rear sheet and the absorbent polymer particles absorbing the liquid excretions and being placed in between the third front sheet and the third rear sheet;

the third front sheet and the third rear sheet are connected with third junctions extending in the longitudinal direction at predetermined intervals in the width direction and fourth junctions extending in the width direction at predetermined intervals in the longitudinal direction when viewed in plan;

the third junctions are arranged to opposite sections of opening sections of the outer absorbent pad; and the opening sections are layered on the third junctions when viewed in plan.

6. The absorbent pad of claim 1, wherein the opening sections are formed in the rectangle configurations and the long sides of the rectangles are provided along with the first junctions when viewed in plan.

7. The absorbent pad of claim 6, wherein the dimension of the long side of the rectangles is formed longer than the width in the longitudinal direction of the second junctions when viewed in plan.

8. The absorbent pad of claim 7, wherein:

the outer absorbent pad is formed with a liquid-permeable second front sheet, a liquid-permeable or liquid-impermeable second rear sheet and absorbent core constituting pulp fibers and absorbent polymer particles absorbing liquid excretions and being placed in between the second front sheet and the second rear sheet;

high fiber density areas are arranged with higher pulp fiber density than the adjacent sections to the opposite sites of the opening sections of the outer absorbent pad; and the opening sections are layered on the high fiber density areas when viewed in plan.

9. The absorbent pad of claim 7, wherein:

the outer absorbent pad is formed with a liquid-permeable third front sheet, a liquid-permeable or liquid-impermeable third rear sheet and the absorbent polymer particles absorbing the liquid excretions and being placed in between the third front sheet and the third rear sheet;

the third front sheet and the third rear sheet are connected with third junctions extending in the longitudinal direction at predetermined intervals in the width direction and fourth junctions extending in the width direction at predetermined intervals in the longitudinal direction when viewed in plan;

the third junctions are arranged to opposite sections of opening sections of the outer absorbent pad; and the opening sections are layered on the third junctions when viewed in plan.

10. The absorbent pad of claim 6, wherein:

the outer absorbent pad is formed with a liquid-permeable second front sheet, a liquid-permeable or liquid-impermeable second rear sheet and absorbent core constituting pulp fibers and absorbent polymer particles absorbing liquid excretions and being placed in between the second front sheet and the second rear sheet;

high fiber density areas are arranged with higher pulp fiber density than the adjacent sections to the opposite sites of the opening sections of the outer absorbent pad; and the opening sections are layered on the high fiber density areas when viewed in plan.

11. The absorbent pad of claim 6, wherein:

the outer absorbent pad is formed with a liquid-permeable third front sheet, a liquid-permeable or liquid-impermeable third rear sheet and the absorbent polymer particles absorbing the liquid excretions and being placed in between the third front sheet and the third rear sheet;

the third front sheet and the third rear sheet are connected with third junctions extending in the longitudinal direction at predetermined intervals in the width direction and fourth junctions extending in the width direction at predetermined intervals in the longitudinal direction when viewed in plan;

the third junctions are arranged to opposite sections of opening sections of the outer absorbent pad; and the opening sections are layered on the third junctions when viewed in plan.

12. The absorbent pad of claim 1, wherein the outer absorbent pad is formed with a liquid-permeable second front sheet, a liquid-permeable or liquid-impermeable second rear sheet and absorbent core constituting pulp fibers and absorbent polymer particles absorbing liquid excretions and being placed in between the second front sheet and the second rear sheet;

high fiber density areas are arranged with higher pulp fiber density than the adjacent sections to the opposite sites of the opening sections of the outer absorbent pad; and the opening sections are layered on the high fiber density areas when viewed in plan.

13. The absorbent pad of claim 1, wherein the outer absorbent pad is formed with a liquid-permeable third front sheet, a liquid-permeable or liquid-impermeable third rear sheet and the absorbent polymer particles absorbing the liquid excretions and being placed in between the third front sheet and the third rear sheet;
- the third front sheet and the third rear sheet are connected with third junctions extending in the longitudinal direction at predetermined intervals in the width direction and fourth junctions extending in the width direction at predetermined intervals in the longitudinal direction when viewed in plan;
- the third junctions are arranged to opposite sections of opening sections of the outer absorbent pad; and
- the opening sections are layered on the third junctions when viewed in plan.

\* \* \* \* \*